(12) United States Patent
Souchay

(10) Patent No.: US 9,955,932 B2
(45) Date of Patent: May 1, 2018

(54) APPARATUS AND METHOD FOR TOMOSYNTHESIS IMAGE ACQUISITION

(71) Applicant: General Electric Company

(72) Inventor: Henri Souchay, Versailles (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 45 days.

(21) Appl. No.: 14/520,929

(22) Filed: Oct. 22, 2014

(65) Prior Publication Data

US 2016/0113607 A1    Apr. 28, 2016

(51) Int. Cl.
A61B 6/00    (2006.01)
A61B 6/02    (2006.01)

(52) U.S. Cl.
CPC .......... A61B 6/4452 (2013.01); A61B 6/025 (2013.01); A61B 6/502 (2013.01)

(58) Field of Classification Search
CPC ........ A61B 6/025; A61B 6/4452; A61B 6/502
See application file for complete search history.

(56) References Cited

U.S. PATENT DOCUMENTS

| 5,594,769 | A | 1/1997 | Pellegrino et al. |
| 5,872,828 | A | 2/1999 | Nikalson et al. |
| 5,999,836 | A | 12/1999 | Nelson et al. |
| 6,282,264 | B1 | 8/2001 | Smith et al. |
| 6,754,298 | B2 | 6/2004 | Fessler |
| 6,940,943 | B2 | 9/2005 | Claus et al. |
| 7,110,490 | B2 | 9/2006 | Eberhard et al. |
| 7,212,606 | B2 | 5/2007 | Souchay et |
| 7,330,529 | B2 | 2/2008 | Kautzer et al. |
| 8,207,736 | B2 | 6/2012 | Chu et al. |
| 8,229,199 | B2 | 7/2012 | Chen et al. |
| 8,246,543 | B2 | 8/2012 | Johnson et al. |
| 8,284,894 | B2 | 10/2012 | Poorter |
| 8,340,388 | B2 | 12/2012 | Rosenstengel |
| 2004/0109529 | A1* | 6/2004 | Eberhard ............... A61B 6/025 378/23 |
| 2008/0095420 | A1 | 4/2008 | Ohyu et al. |
| 2008/0267484 | A1 | 10/2008 | Chen |

(Continued)

FOREIGN PATENT DOCUMENTS

| CN | 102867294 A | 1/2013 |
| WO | 2008085577 A2 | 7/2008 |
| WO | 2014011681 | 1/2014 |

OTHER PUBLICATIONS

International Search Report and Written Opinion for corresponding WO Appln. No. PCT/US2015/056463, dated Jan. 21, 2016, 11 pages.

(Continued)

Primary Examiner — Dani Fox
(74) Attorney, Agent, or Firm — Grogan, Tuccillo & Vanderleeden, LLP

(57) ABSTRACT

A method for image acquisition includes selectively concealing and exposing an x-ray source to a target object while the x-ray source travels along a first path and moving an x-ray detector along a second path in a first direction while the x-ray source is exposed to the target object. The method further includes moving the x-ray detector along the second path in a second direction generally opposite the first direction while the x-ray source is concealed from the target object.

20 Claims, 3 Drawing Sheets

(56) References Cited

U.S. PATENT DOCUMENTS

| | | |
|---|---|---|
| 2009/0022264 A1 | 1/2009 | Zhou et al. |
| 2010/0128958 A1 | 5/2010 | Chen et al. |
| 2010/0284596 A1 | 11/2010 | Miao et al. |
| 2010/0303202 A1 | 12/2010 | Ren et al. |
| 2011/0188624 A1 | 8/2011 | Ren et al. |
| 2012/0140878 A1 | 6/2012 | Souchay |
| 2012/0224664 A1 | 9/2012 | Maack |
| 2014/0140472 A1 | 5/2014 | Hemmendorff et al. |

OTHER PUBLICATIONS

Lyuboshenko et al., "Stable Signal and Image Reconstruction from Noisy Fourier Transform Phase", IEEE Transactions on Signal Processing, vol. No. 47, Issue No. 1, pp. 244-250, Jan. 1999.

Zhou et al., "Application of Fourier—Wavelet Regularized Deconvolution for Improving Image Quality of Free Space Propagation X-ray Phase Contrast Imaging", Physics in Medicine Biology, vol. No. 57, pp. 7459-7479, 2012.

PCT Search Report and Written Opinion issued in Connection With Related PCT Application No. PCT/US2015/030672 dated Sep. 15, 2015.

European Search Report and Opinion issued in Connection With Related EP Application No. 16181523.8 dated Dec. 9, 2016.

\* cited by examiner

APPARATUS AND METHOD FOR TOMOSYNTHESIS IMAGE ACQUISITION

BACKGROUND

Technical Field

Embodiments of the invention relate generally to image acquisition. Particular embodiments relate to x-ray imaging systems used for mammography.

Discussion of Art

Generally, x-ray imaging systems expose an x-ray detector, e.g., gamma photon scintillator or film, to an x-ray source, via a target object that is to be imaged. Attenuation or dispersion of photons emitted from the x-ray source within the target object produces a variegated image at the x-ray detector. This image then can be processed to ascertain radiopacity at various regions of the target object. For example, in mammography, where breast tissue is imaged, a region of higher than average radiopacity is understood to indicate the presence of a potentially pre-cancerous or cancerous lesion.

In medical imaging, it is generally desirable to minimize the size and intensity of an x-ray source, especially when imaging radiation-sensitive tissues such as breast tissue. In particular, it is desirable to minimize the radiation exposure needed to identify and localize, in three dimensions, regions of high radiopacity that could indicate precancerous cells. To accomplish this, a moving x-ray source may be used to provide a low x-ray dose to the target tissue while also obtaining volumetric detector data for use in localizing regions of high radiopacity. A moving x-ray source, however, presents a potential problem of image distortion along the x-ray source direction of motion.

As mentioned, it is also desirable to identify radiopaque areas in three dimensions. Describing or displaying a three-dimensional structure from a sequence of planar images obtained from different perspectives is referred to as "tomosynthesis." The quality of tomosynthesis solutions depends upon the quantity and quality of planar images and on the total angle covered by the planar image array.

Tomosynthesis solutions generally can be categorized as "sharp" (providing relatively high resolution and fidelity of location within three dimensions) or "fast" (providing real-time or near-real-time imaging). For some types of medical imaging, such as mammography, sharp or fast solutions are exclusive choices. Fast tomosynthesis involves continuous source motion during exposure, therefore reducing signal transfer at higher frequencies, and loss of information, which precludes obtaining optimally sharp images. The fuzziness of fast tomosynthesis can be mitigated to some extent by a moving x-ray detector, however the final travel distance required for the detector eventually affects the possible imaging area due to positioning constraints of the patient/organ relative to the x-ray detector.

With reference to positioning constraints, it is desirable in medical imaging generally, and especially in mammography, to minimize the size of the imaging equipment that must be juxtaposed to a patient's body. Reducing the size of imaging equipment present a problem of constraining x-ray source movement, which detracts from the clarity of tomosynthesis solutions for the reasons discussed above. Reducing the size of imaging equipment also can constrain x-ray detector movement, which also can detract from the clarity of tomosynthesis as further discussed below.

For continuous detector motion, the x-ray detector travel distance proper to compensate apparent source size is estimated from $\frac{1}{10}$th to $\frac{1}{5}$th of the tube linear distance. For example, for a typical prior art tube travel of 16 cm) (+/−7.5°), the resulting x-ray detector trajectory is >16 mm, which could impact breast positioning. For further tube travel (+/−12.5°→27 mm detector travel) it becomes fairly impractical to compress to cover the imaging apparatus field of view.

In view of the above, it is desirable to provide apparatus and methods for moving source mammography that mitigates image distortion and apparatus volume envelope. Such apparatus and methods might also be helpful toward volumetric x-ray imaging, generally.

BRIEF DESCRIPTION

In embodiments, a method for image acquisition includes selectively concealing and exposing an x-ray source to a target object while the x-ray source travels along a first path and moving an x-ray detector along a second path in a first direction while the x-ray source is exposed to the target object. The method further includes moving the x-ray detector along the second path in a second direction generally opposite the first direction while the x-ray source is concealed from the target object.

In other embodiments, an apparatus for image acquisition includes an x-ray source moveable about a first path with reference to a target object and an x-ray detector moveable about a second path with reference to the target object. The apparatus further includes a controller configured to selectively expose the x-ray source to the target object and conceal the x-ray source from the target object while the x-ray source is travelling about the first path, and move the x-ray detector along the second path in a first direction while the x-ray source is exposed, and a second direction, generally opposite to the first, when the x-ray source is concealed.

DRAWINGS

The present invention will be better understood from reading the following description of non-limiting embodiments, with reference to the attached drawings, wherein below:

DETAILED DESCRIPTION

Figure 1:
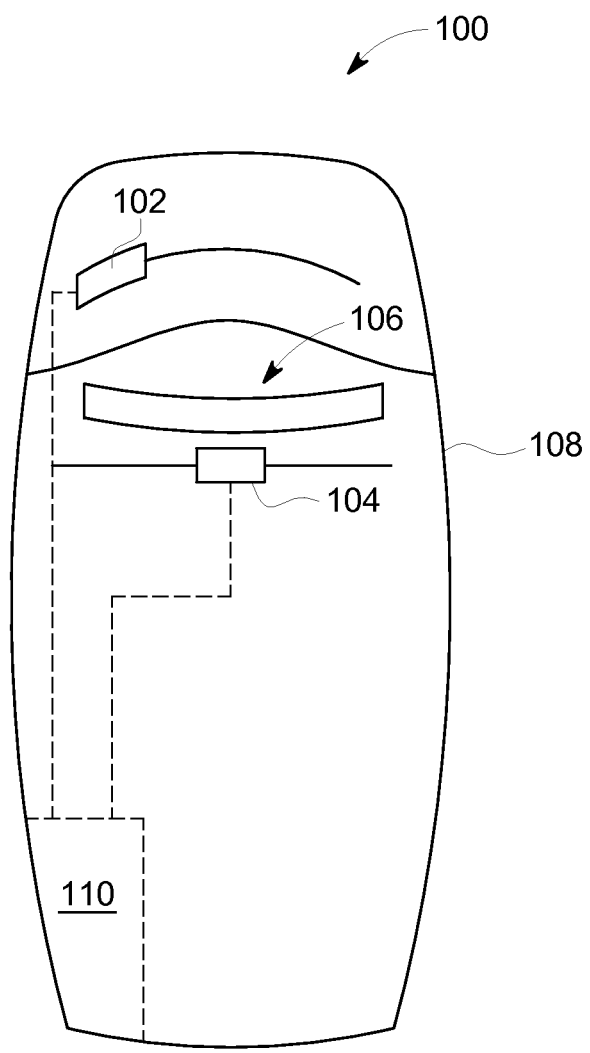
FIG. 1 shows schematically a mammographic apparatus according to an embodiment of the invention.

Reference will be made below in detail to exemplary embodiments of the invention, examples of which are illustrated in the accompanying drawings. Wherever possible, the same reference characters used throughout the drawings refer to the same or like parts, without duplicative description. Although exemplary embodiments of the present invention are described with respect to mammography, embodiments of the invention also are applicable for use in volumetric imaging, generally. As will be appreciated, embodiments of the present invention may be used to analyze animal tissue generally and are not limited to human tissue.

As used herein, the terms "substantially," "generally," and "about" indicate conditions within reasonably achievable manufacturing and assembly tolerances, relative to ideal desired conditions suitable for achieving the functional purpose of a component or assembly.

A mammographic apparatus 100, according to embodiments of the invention, is shown in FIG. 1. The apparatus 100 includes an x-ray source 102, an x-ray detector 104, and a target receptacle 106 that is disposed between the x-ray source and the x-ray detector. The x-ray source 102, the x-ray detector 104, and the target receptacle 106 also are mounted on a stand 108. A target object (not shown) can be received into the target receptacle 106 for imaging by operation of the x-ray source 102 and the x-ray detector 104. The x-ray source 102 and the x-ray detector 104 are movably mounted on the stand 108 by way of motors or other actuators (not shown). The mammographic apparatus 100 also includes a controller 110, which is housed within the stand 108. The controller 110 coordinates the motors and/or actuators (not shown) in order to implement movement of the x-ray source 102 and of the x-ray detector 104, according to a mammography sequence as further discussed below.

Although in many embodiments of the invention, and as described above, the controller 110 may be in the nature of a motor controller, i.e. incorporating a general purpose processor that is configured by software to adjust the speed and direction of one or more motors or actuators. In other embodiments, the controller may incorporate one or more mechanisms that physically constrain the movements of the x-ray detector to correspond with movements of the x-ray source as further discussed below with reference to FIGS. 2A-2B, 3, and 4.

Figure 2A:
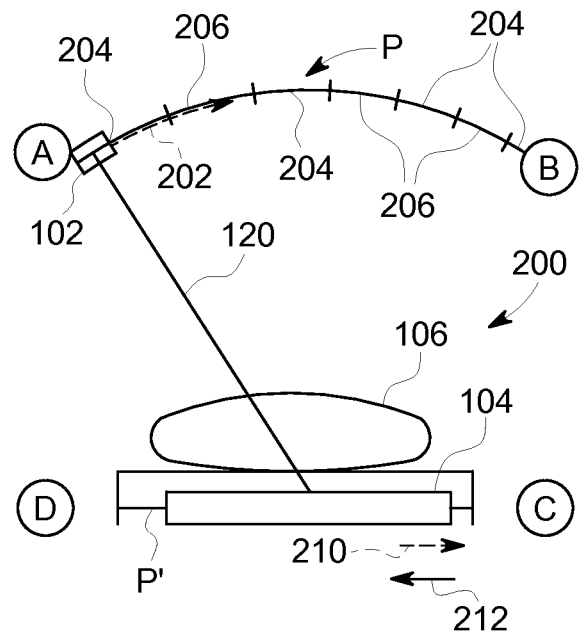
FIGS. 2A-2B show schematically a method of operating the apparatus shown in FIG. 1.
Figure 2B:
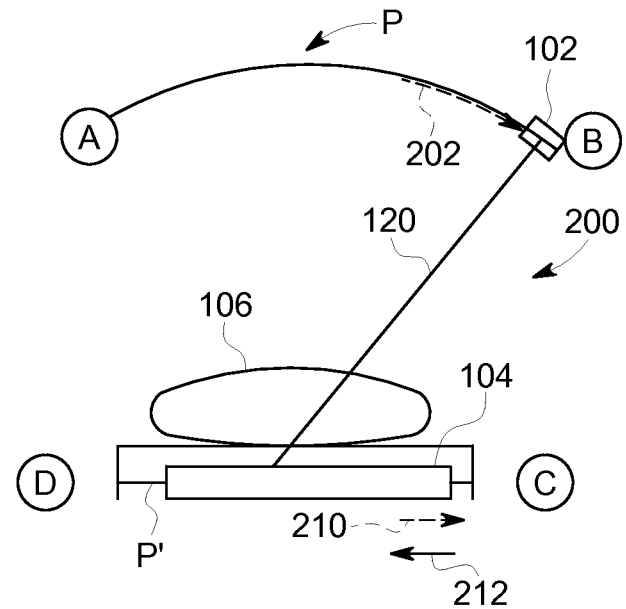

Referring to FIGS. 2A and 2B, during a mammography sequence 200, according to aspects of the invention, the controller 110 implements movement 202 of the x-ray source 102 along a first path P, e.g., from a first position A toward a second position B. The total movement 202 may be continuous (scanning) or intermittent (snapshot). Embodiments in which the total movement 202 is a scanning movement advantageously reduce acceleration loads and cycles for which the x-ray source driver (not shown) must be designed. Although shown as arcuate, the path P, and movement 202, may be linear or plane-wise, e.g. sawtooth or curvilinear translational movement across a plane.

During the movement 202, the x-ray source 102 is intermittently exposed and concealed to the target receptacle 106 and the x-ray detector 104. In particular, the movement 202 comprises a first plurality of intervals 204 when the x-ray source 102 is exposed, as well as a second plurality of intervals 206 when the x-ray source is concealed. In order to enhance speed of operation and localization of radiopaque regions, at least the exposure intervals 204 provide continuous movement, in a "scanning" fashion without interruption or pauses.

According to certain embodiments, the concealment intervals 206 also provide continuous movement, so as to achieve the advantages of a total scanning movement 202 of the x-ray source 102 as discussed above. Although the exposure and concealment intervals 204, 206 are shown of generally equal length, they need not be equal in length and indeed a scanning movement can be accomplished with either type of interval being of arbitrary non-zero length.

In addition to movement of the x-ray source 102, as described above, the controller 110 also implements movement 208 of the x-ray detector 104 along a second path P' from a third position C toward a fourth position D and back. In embodiments, the controller 110 coordinates movement of the x-ray detector with the scanning movement 202 of the x-ray source 102. During exposure intervals 204, the x-ray detector moves generally along the second path in a first direction 212, i.e. from the third position C toward the fourth position D. During concealment intervals 206, the x-ray detector 104 is moved along the second path P' in a second direction 210 that is generally opposite the first direction, i.e. from the fourth position D back toward the third position C. Through this process, the controller 110 may implement a generally oscillating motion of the x-ray detector 104. It is not required, however, that the x-ray detector 104 retrace each movement 212 during each movement 210. For example, in embodiments, during at least one of its returning movements along the second path in the second direction, the x-ray detector 104 may be moved in a side stepping fashion, i.e., generally orthogonal to the first and second directions, so that in that movement 210 the x-ray detector displaces toward or away from the view of FIGS. 2A and 2B. Also, although the movements 210, 212 are shown as linear, the x-ray detector 104 may be moved in arcuate fashion about a common center with the x-ray source 102. Arcuate motion about a common center advantageously optimizes the apparent size of the x-ray source 102 to the x-ray detector 104.

In use, during exposure intervals 204, the controller 110 coordinates the movements 212 of the x-ray detector 104 in order to match the plurality of scanning movements 204 of the x-ray source 102, thereby minimizing variations of an apparent size of the x-ray source 102 to the x-ray detector 104 throughout the exposure intervals 204. On the other hand, during concealment intervals 206, the controller 110 coordinates the movements 210 of the x-ray detector 104 in order to reposition the x-ray detector relative to a photon beam 120 from the x-ray source 102, thereby allowing for multiple poses of the target object within a smaller volume envelope than would be achievable by continuous unidirectional movement of the x-ray detector 104. The repositioning movements 210 can be directly oscillating, straight back toward the third position C; alternatively, the repositioning movements can be offset, so that the multiple poses are side-by-side rather than aligned along a line. In other embodiments the repositioning movements 210 can be more complex, e.g., curvilinear or elliptical.

In FIG. 2A, an embodiment of the inventive apparatus 100 is presented in schematic view at the beginning of the sequence 200. In FIG. 2B, the inventive apparatus 100 is presented in schematic view at the end of the sequence 200. Overall, the x-ray detector 104 has very limited motion, which is coordinated with the movement of the exposed x-ray source 102 so that, during the exposure intervals 204, the apparent size of the x-ray source 102 as seen from the x-ray detector 104 through a fixed region of the target object, is preserved.

In other words, during each of the exposure intervals 204, the x-ray source 102 and the x-ray detector 104 are moved together (respectively, from A toward B and from C toward D) so that the photon beam 120 from the x-ray source, through the target object, continuously strikes a same region on the x-ray detector. So, if for example the x-ray source 102 is moved through a translational exposure interval 204 at a constant speed a, then the x-ray detector 104 concurrently is moved through an opposite translational movement 212 according to a speed law $(v*d(t)=a)$ for each of the plurality of exposure intervals 204 wherein the x-ray photon beam 120 is ON. Contrarily, if for example the x-ray source 102 is moved through a translational concealment interval 206 at a constant speed b (typically, b=a), then for the x ray detector 104 $(v*d(t)=-b)$, with b positive constant, for each of the plurality of concealment intervals 206 wherein the x-ray photon beam 120 is OFF.

Taking "TON" as the sum of time during exposure intervals 204 of the x-ray source 102, and "TOFF" as the sum of time during concealment intervals 206, then (TON*a) is the distance moved by the x-ray detector from position C toward position D along the first direction during movements 212; (TOFF*b) is the distance moved by the x-ray detector from position D toward position C along the second direction during movements 210. In order to minimize the space within which the x-ray detector 204 must travel, the controller should implement an algorithm in which (TON*a=TOFF*b). Minimization of space around the x-ray detector 204 is generally desirable in medical imaging apparatus for ergonomic issues, and is especially desirable in mammography apparatus 100.

Figure 3:
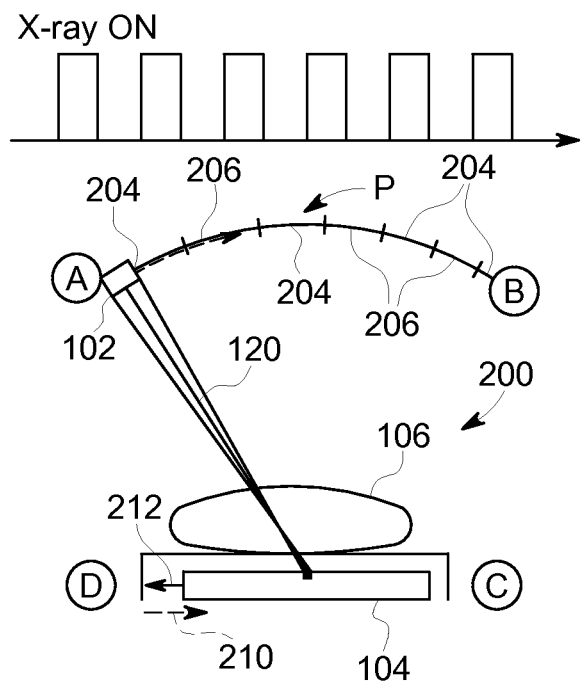
FIGS. 3 and 4 show schematically additional details of operating the inventive apparatus and method.
Figure 4:
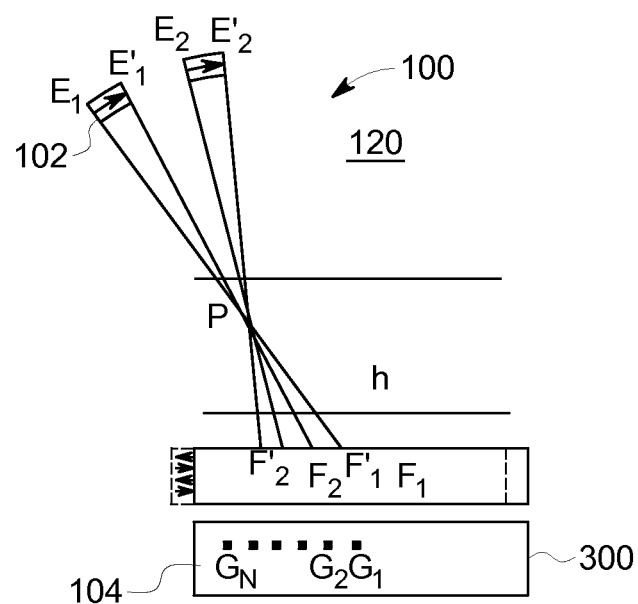

FIGS. 3 and 4 show schematically the inventive apparatus 100, with the x-ray source 102 being used in one or more scanning movements E-E' to image onto the x-ray detector 104 a target object, which includes a point of interest P disposed at a height h above the x-ray detector. FIG. 4, specifically, shows a "system referential" schematic of the segments F-F' that are defined by the photon beam 120 with reference to the target object, as the photon beam passes through the point of interest P during scanning motion of the x-ray source 102. Also in FIG. 4, below the system referential schematic, is a "detector referential" schematic that shows the image(s) G that are produced on the x-ray detector by the photon beam.

Advantageously, because the x-ray detector 104 oscillates back from D toward C during each of the concealment intervals 206, then during each of the exposure intervals 204 (movements E1-E1', E2-E2', . . . En-En'), the photon beam 120 from the x-ray source 102 lingers at a different point G1, G2, . . . Gn on the x-ray detector 104, even in case the x-ray detector completely or partially retraces the second path. This has a surprisingly advantageous result that a localized defect of the x-ray detector 104 need not prevent accurate imaging of the target object, which is a potential problem with some prior art arrangements. Instead, as shown at right in FIG. 3, any localized defect can be mitigated by obtaining multiple images G1, G2, . . . Gn, such that each portion of the target can be imaged on a non-defective region of the x-ray detector 104. As another surprising advantage of the inventive apparatus, still referring to FIG. 3, a point of interest P can be located at a height h within the target object, based on an assessment of spacing among the multiple images G1 . . . Gn of the point of interest as produced on the x-ray detector 104 within the multiple poses of the target object.

As another advantage, oscillating detector motion enables the x-ray detector assembly to fit within a smaller envelope than is required by prior art apparatus; in particular, the lateral envelope for the x-ray detector assembly (along the general extent of the second path) may be smaller than the lateral envelope for the x-ray source assembly. Thus, it is possible to reduce maximum required power of the x-ray source and also reduce maximum acceleration requirement of the x-ray source positioning assembly. Additionally, having a lower x-ray source power requirement permits using a lighter weight x-ray tubehead, which in combination with a reduced acceleration requirement results in significantly reduced structural requirements for the x-ray source positioner. Furthermore, oscillating detector motion permits moving the x-ray source fewer times per imaging sequence, thus reducing positioner reliability requirements. Also, fewer x-ray source moves result in shorter scan times, with improved patient comfort (breath-holding time reduced from about 10 to about 15 seconds, down to about 2 to about 3 seconds); and also enhances image quality due to reduced risk of patient motion during the breath-holding time. Moreover, reducing the lateral envelope for the x-ray detector assembly is particularly advantageous for mammography, as an excessive lateral envelope can present challenges in positioning a target object within the target receptacle 106.

Thus, embodiments of the invention implement a method for image acquisition, which includes selectively concealing and exposing an x-ray source to a target object while the x-ray source travels along a first path; moving an x-ray detector along a second path in a first direction while the x-ray source is exposed to the target object, and moving the x-ray detector along the second path in a second direction generally opposite the first direction while the x-ray source is concealed from the target object. In certain embodiments, the method may include moving the x-ray detector along the second path at an opposite linear velocity as the x-ray source when the x-ray source is exposed to the target object, and moving the x-ray detector along the second path at a same linear velocity as the x-ray source when the x-ray source is concealed from the target object. The first path may be generally arcuate about an axis that is disposed between the x-ray source and the x-ray detector. In certain embodiments, the method may include moving the x-ray detector about the axis at a same angular velocity as the x-ray source when the x-ray source is exposed to the target object, and moving the x-ray detector about the axis at an opposite angular velocity as the x-ray source when the x-ray source is concealed from the target object. The method may also include assessing at least one spacing among multiple images of a point of interest on the x-ray detector; and locating the point of interest at a height above the x-ray detector, based on the at least one assessed spacing. The second path may include at least one side stepping movement, and, if so, the side stepping movements may correspond to when the x-ray source is concealed from the target object. In some embodiments, the selective concealing and exposing an x-ray source to a target object, while the x-ray source travels along the first path, occurs in respective pluralities of first and second intervals.

Embodiments of the invention provide an apparatus for image acquisition, which includes an x-ray source that is moveable about a first path with reference to a target object; an x-ray detector that is moveable about a second path with reference to the target object; and a controller configured to selectively expose the x-ray source to the target object and conceal the x-ray source from the target object while the x-ray source is travelling about the first path, and to move the x-ray detector along the second path in a first direction while the x-ray source is exposed, and in a second direction, generally opposite to the first, when the x-ray source is concealed. The first path may be generally arcuate about an axis that is disposed between the x-ray source and the x-ray detector. The second path may be generally linear with the first direction generally contrary to the movement of the x-ray source, while the second direction is generally aligned with the movement of the x-ray source. Alternatively, the second path may be generally arcuate about the same axis of the first path, moving the x-ray detector along the second path at a same angular velocity as the x-ray source when the x-ray source is exposed, and moving the x-ray detector along the second path at an opposite angular velocity as the x-ray source when the x-ray source is concealed. The controller may be further configured to assess at least one spacing among multiple images of a point of interest on the x-ray detector, and to locate the point of interest at a height above the x-ray detector, based on the at least one assessed spacing. In certain embodiments, the second path fits into a smaller lateral envelope than does the first path. The second path may include one or more side stepping movements, and, if so, the side stepping movements may correspond to when the x-ray source is concealed. The controller may be housed within a stand supporting the x-ray source, the target receptacle, and the x-ray detector. The controller may incorporate a mechanism for coordinating the movements of the x-ray source and the x-ray detector along their respective first and second paths. The controller may incorporate a processor that is programmed to coordinate the movements of the x-ray source and the x-ray detector along their respective first and second paths.

Other embodiments of the invention provide an article, which includes computer-readable media encoded with image data that was obtained from an x-ray detector during a process that includes selectively exposing an x-ray source to a target object and concealing the x-ray source from the target object while the x-ray source travels along a first path at one side of the target object, and concurrently moving the x-ray detector along a second path at the opposite side of the target object, wherein the x-ray detector was moved in a first direction while the x-ray source was exposed, and in a second direction, generally opposite to the first, while the x-ray source was concealed.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice embodiments of the invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal language of the claims.

As used herein, an element or step recited in the singular and proceeded with the word "a" or "an" should be understood as not excluding plural of the elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described method and apparatus, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method for image acquisition comprising:
   selectively concealing and exposing an x-ray source to a target object while the x-ray source travels along a first path;
   moving an x-ray detector along a second path in a first direction while the x-ray source is exposed to the target object;
   moving the x-ray detector along the second path in a second direction generally opposite the first direction at a same linear velocity as the x-ray source while the x-ray source is concealed from the target object; and
   wherein a center of a photon beam from the x-ray source impinges on different locations on the x-ray detector from different x-ray exposure positions as the x-ray source travels along the first path.

2. The method as claimed in claim 1, wherein the x-ray detector is moved along the second path at an opposite linear velocity as the x-ray source when the x-ray source is exposed to the target object.

3. The method as claimed in claim 1, wherein the first path is generally arcuate about an axis that is disposed between the x-ray source and the x-ray detector.

4. The method as claimed in claim 3, further comprising:
   moving the x-ray detector about the axis at a same angular velocity as the x-ray source when the x-ray source is exposed to the target object; and
   moving the x-ray detector about the axis at an opposite angular velocity as the x-ray source when the x-ray source is concealed from the target object.

5. The method as claimed in claim 1, further comprising:
   assessing at least one spacing among multiple images of a point of interest on the x-ray detector; and
   locating the point of interest at a height above the x-ray detector, based on the at least one assessed spacing.

6. The method as claimed in claim 1, wherein the second path includes at least one side stepping movement.

7. The method as claimed in claim 6, wherein the side stepping movements correspond to when the x-ray source is concealed from the target object.

8. The method of claim 1, wherein the selective concealing and exposing an x-ray source to a target object, while the x-ray source travels along the first path, occurs in a plurality of respective first and second intervals.

9. An apparatus for image acquisition comprising:
   an x-ray source moveable about a first path with reference to a target object;
   an x-ray detector moveable about a second path with reference to the target object;
   a controller configured to selectively expose the x-ray source to the target object and conceal the x-ray source from the target object while the x-ray source is travelling about the first path, and move the x-ray detector along the second path in a first direction while the x-ray source is exposed, and in a second direction, generally opposite to the first, at a same linear velocity as the x-ray source when the x-ray source is concealed; and wherein a center of a photon beam from the x-ray source impinges on different locations on the x-ray detector from different x-ray exposure positions as the x-ray source travels along the first path.

10. The apparatus as claimed in claim 9, wherein the first path is generally arcuate about an axis that is disposed between the x-ray source and the x-ray detector.

11. The apparatus as claimed in claim 9, wherein the second path is generally linear and the first direction is generally contrary to the movement of the x-ray source, while the second direction is generally aligned with the movement of the x-ray source.

12. The apparatus as claimed in claim 11, wherein the second path is generally arcuate about the same axis of the first path, moving the x-ray detector along the second path at a same angular velocity as the x-ray source when the x-ray source is exposed, and moving the x-ray detector along the second path at an opposite angular velocity as the x-ray source when the x-ray source is concealed.

13. The apparatus as claimed in claim 9, the controller further configured to assess at least one spacing among multiple images of a point of interest on the x-ray detector, and to locate the point of interest at a height above the x-ray detector, based on the at least one assessed spacing.

14. The apparatus as claimed in claim 9, wherein the second path fits into a smaller lateral envelope than does the first path.

15. The apparatus as claimed in claim 9, wherein the second path includes one or more side stepping movements.

16. The apparatus as claimed in claim 15, wherein the side stepping movements correspond to when the x-ray source is concealed.

17. The apparatus as claimed in claim 9, wherein the controller is housed within a stand supporting the x-ray source, the target receptacle, and the x-ray detector.

18. The apparatus as claimed in claim 9, wherein the controller incorporates a mechanism for coordinating the movements of the x-ray source and the x-ray detector along their respective first and second paths.

19. The apparatus as claimed in claim 9, wherein the controller incorporates a processor that is programmed to coordinate the movements of the x-ray source and the x-ray detector along their respective first and second paths.

20. A method for image acquisition comprising:
selectively concealing and exposing an x-ray source to a target object while the x-ray source travels along a first path;
moving an x-ray detector along a second path in a first direction while the x-ray source is exposed to the target object,
moving the x-ray detector along the second path in a second direction generally opposite the first direction at a same linear velocity as the x-ray source while the x-ray source is concealed from the target object;
assessing at least one spacing among multiple images of a point of interest on the x-ray detector, and
locating the point of interest at a height above the x-ray detector, based on the at least one assessed spacing;
wherein a center of a photon beam from the x-ray source impinges on different locations on the x-ray detector from different x-ray exposure positions as the x-ray source travels along the first path.

* * * * *